United States Patent [19]
Karp et al.

[11] Patent Number: 5,515,852
[45] Date of Patent: May 14, 1996

[54] METHOD AND APPARATUS FOR A DETECTION STRENGTH SPATIAL FILTER IN AN ULTRASOUND IMAGING SYSTEM

[75] Inventors: Sydney M. Karp, Reading; Jerome F. Witt; Raymond A. Beaudin, both of Andover, all of Mass.

[73] Assignee: Hewlett-Packard Company, Palo Alto, Calif.

[21] Appl. No.: 254,100

[22] Filed: Jun. 6, 1994

[51] Int. Cl.[6] ................... A61B 8/00; A61B 8/06
[52] U.S. Cl. ................... 128/660.07; 128/661.09
[58] Field of Search ................ 128/660.01, 660.07, 128/661.10, 661.09–661.10; 73/625–626, 602; 364/413.25

[56] References Cited

U.S. PATENT DOCUMENTS

| | | | |
|---|---|---|---|
| 4,850,364 | 7/1989 | Leavitt | 128/661.09 |
| 4,928,231 | 5/1990 | Hunt et al. | 364/518 |
| 5,105,814 | 4/1992 | Drukarey et al. | 128/660.07 |
| 5,111,823 | 5/1992 | Cohen | 128/660.07 |
| 5,257,624 | 11/1993 | Frazer et al. | 128/660.01 |
| 5,299,577 | 4/1994 | Brown et al. | 128/660.07 |

*Primary Examiner*—Francis Jaworski
*Attorney, Agent, or Firm*—Edward L. Miller

[57] ABSTRACT

An ultrasound imaging system where a location in the image has associated with it an amplitude and a velocity derived from a doppler shift assigns a detection strength to each location. Detection strength is a mapping from each possible combination of the amplitude and velocity into a scalar value that represents the likelihood that the velocity is not an artifact of the noise in the environment. The detection strength values are spatially filtered and then used to determine whether to accept or reject the measured velocity. A more optimistic filtering strategy for the measured velocity is now possible, and cooperates with a filtered detection strength to trim away suspicious regions in the image. The filtered detection strength signal can be used to compensate for unwanted side effects of other filtering done during the processing of the measured parameters. When the number of input bits exceeds the address space of a ROM filtering digital representations of measured parameters, the input values can be bifurcated into MSB's and LSB's, with the MSB's applied to the ROM as the address. The LSB's are sent to a MUX. The output value produced by each input combination can include two fields, one of which is the filtered or transformed value of the applied MSB's, and the other of which is a selector field. The selector field is pre-encoded to direct the MUX to select the LSB's that ought to be associated with the filtered or transformed value produced by the ROM in the other field. These recovered LSB's are then conjoined or otherwise used with that filtered or transformed value. The corduroy artifact of parallel flow operation can be removed by incorporating into the lateral detection strength filter a weighting scheme wherein the sum of the weights for the odd numbered radials in the filter's aperture equals the sum of the weights for the even numbered radials in the filter's aperture.

2 Claims, 12 Drawing Sheets

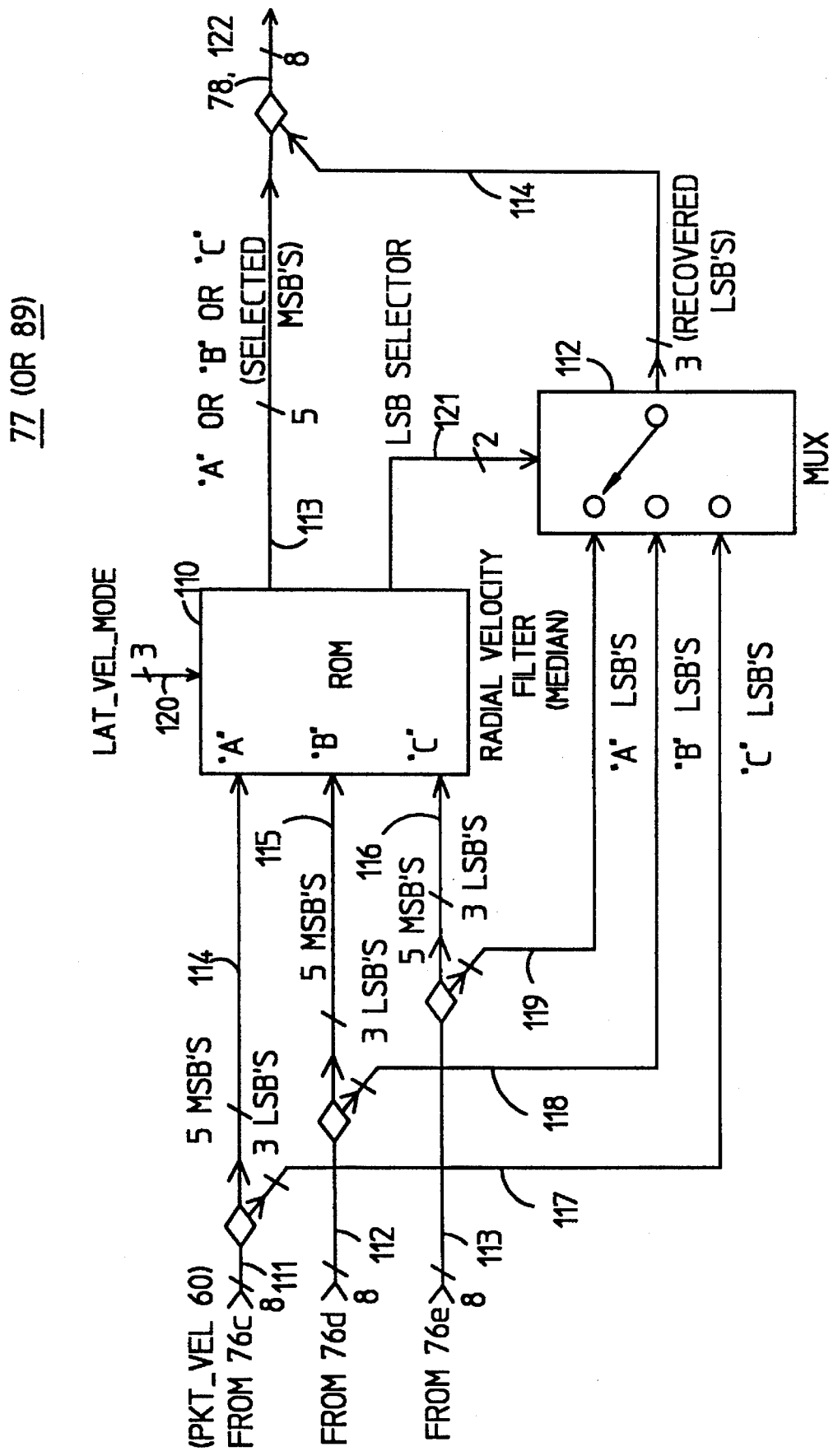

5,515,852

METHOD AND APPARATUS FOR A DETECTION STRENGTH SPATIAL FILTER IN AN ULTRASOUND IMAGING SYSTEM

BACKGROUND OF THE INVENTION

Ultrasound imaging is a non destructive and noninvasive way of examining structures concealed from ordinary visual inspection; e.g., organs within a living creature, such as the human body. For an appreciation of the overall environment in which the invention is of benefit, refer now to FIGS. 1A–C, wherein an ultrasound imaging unit 1 is shown having an untrasound probe 2 coupled thereto by a cable 3 for forming an image (not shown) upon a CRT 4 of an organ 5 beneath an exterior layer of skin (also not shown). To do this the probe 2 is brought into contact with the layer of skin. Ultrasonic transducer elements (7, 8, . . . 9) within the probe 2 emit "beams" of ultrasound 6. A beam is a short burst of ultrasonic acoustic energy traveling along a direction in which the probe 2 is generally oriented. The ultrasound beams are emitted one at a time. A given beam 6 may be emitted several times in succession prior to the emitting of an adjacent beam, which in turn may be emitted several times, and so forth. The acoustic energy in a beam 6 is partially absorbed by tissue within the body as it propagates inward toward the organ 5. Some is absorbed by the organ, while some portions are reflected. Some of what is reflected travels back toward the probe 2 (return beams 10–15), where signals generated in the transducer elements that can be processed to contribute to the formation of an image corresponding to the shape of the organ 5. Some ultrasound systems are equipped to detect a doppler shift in the frequency of the reflected ultrasound energy. The doppler shift is caused by motion within the substance doing the reflecting, e.g., blood within a vessel or the heart. In these systems the doppler shift corresponds to a velocity of interest, and different velocities are represented by different colors.

The more sophisticated ultrasound imaging systems use a phased array of transducers (7, 8 . . . 9) in the probe 2 to steer the ultrasound beam 6 in a direction of interest. For example, the beam 6 depicted in FIG. 1A is not perpendicular to the row of transducers 7–9 in the probe. This steerability is achieved by exciting the transducers 7–9 in the probe 2 at slightly different times, such that cancellation and reinforcement of the outward propagating ultrasound concentrates the ultrasound energy in the desired direction. The various directions are referred to as radials, and if an odd number of transducers were excited to produce a beam along a particular radial the beam or radial is said to be centered on the middle transducer of that odd number. An even number of transducers would produce a beam or radial centered on the midpoint between the two innermost transducers of the even number thereof. The number of transducers excited to produce the beam along a given radial is called the aperture, and the number of transducers in the aperture is generally less than the total number of transducers in the probe 2. As a consequence, the aperture is frequently (although not always) shifted across the surface of the probe 2 as the imaging operation proceeds. (Those familiar with ultrasound imaging equipment for medical applications will recognize that the field of view 16 depicted in FIG. 1A corresponds to a non-shifting aperture.)

Steerability of the beam may be thought of as focusing, and it works also for ultrasound reflected from things within the field of view 16 and subsequently propagating back toward the probe. To focus in the receive case the signals produced by the various transducers in the aperture are selectively delayed and then summed. This allows the probe 2 to listen with much greater sensitivity to reflections originating along a given radial.

The focusing that steers the transmitted beam or sensitivity to reflections actually focuses to a point along the desired radial, rather than to the entire radial itself. In many instances the depth of field is such that adequate definition, or resolving power, is maintained by setting the transmit focal point at some fixed depth. In other instances it is possible to change the transmit focal depth to be either shallower or deeper. During receive the focal point can be continuously adjusted to lie at different depths along the radial upon which the most recent ultrasound burst has been transmitted. This variation in receive depth focusing is performed in real time as the various echoes are returning from along that radial.

The ability to steer the beam allows the field of view 16 to be a sector-shaped section, rather than a simple parallel projection outward from between the transducers on the ends of the probe 2. Steerability can also be used to significantly increase definition and resolving power of items of interest that are squarely within the field of view.

As will be appreciated as the discussion proceeds, each transducer has associated with it an individual signal path that contains a great many other items, such as delays, amplifiers and perhaps switches. Each such signal path and its associated collection of hardware (including the transducer) is commonly referred to as a "channel".

To continue, the ultrasound unit 1 both controls the excitation of the transducer elements within the probe 2 and does the processing necessary to combine the echoes (reflections) into an image. To this end the various transducers (7, 8, . . . 9) in probe 2 are coupled to respective transmit drivers (20, 21, . . . 22) and to respective receive amplifiers (23, 24, . . . 25). A respective collection of transmit delay elements (26, 27, . . . 28) are programmed via a control bus 29 to delay a FIRE_LINE signal 30 by amounts selected to focus the energy of each transducer in the aperture onto a point along the desired radial. The variously delayed FIRE-LINE signals are coupled to their respective transmit drivers (20, 21, . . . 22) whose outputs are high voltage pulses at the desired frequency and which are conveyed by the cable 3 to the transducer elements (7, 8, . . . 9).

When thus excited each transducer produces a short burst of sinusoidal compressional motion that propagates acoustically into the body. Typical frequencies for the acoustic energy are 2.5, 5 and 10 MHz. The focused beam 6 propagates outward from the probe 2 along the desired radial. As different features are encountered various partial reflections are generated. In the figure, for example, dotted lines 10, 11, . . . 12 represent acoustic energy reflected, from the near side of a blood vessel 5, to corresponding channels 1, 2, . . . n. The dot/dashed lines 13, 14, . . . 15 represent acoustic energy reflected a bit later in time from the far side of the blood vessel 5.

Immediately after the transmitted burst reflected acoustic energies reaching the various channels become electrical signals that are amplified by the corresponding receive amplifiers 23, 24, . . . 25. The outputs of the receive amplifiers are coupled to additional corresponding amplifiers 31, 32, . . . 33. To counteract the greater attenuation experienced by echoes originating deeper within the body gain of these additional amplifiers is ramped upwards during receive time, until a limit is reached where the noise floor becomes obtrusive. This ramping is accomplished by gain control line 34. The outputs of these amplifiers are converted to a more convenient intermediate frequency (not shown) and coupled to associated respective programmable delay elements 35, 36, . . . 37. The delayed signal for the channels in the aperture are then summed in a summer 38.

At this point the signal emerging from summer 38 may be likened to an IF signal that possesses a rather complex form of modulation. The center frequency of the IF signal represents (but is not the same as) the frequency of the original sinusoidal burst produced when the transducers were excited at the time the (radial) line was fired. The amplitude represents the degree of reflection from things along the radial, and in the absence of any significant reflection the amplitude may approach zero. The amplitude varies with time as reflections along the radial, occur at different depths. However, since reflections originating deeper within the body are subject to attenuation of the original burst as it propagates outward away from the probe and then again as the reflection propagates back toward the probe, an attempt is made to normalize amplitude by ramping the gain of the receive system as a function of time. This makes amplitude a function of reflection coefficient (of the organ 5) rather than of the depth of where that reflection coefficient occurs. Any deviation in signal frequency from the center frequency indicates motion within the thing doing the reflecting.

Just as in most receivers, it is the modulation that conveys the useful information. What is wanted now is to extract the amplitude variation information and the frequency variation information, and dispense with the IF component. This is accomplished in a known way by mixing (heterodyning) the carrier with local oscillator signals 41 and 42 that are each the same in frequency as the IF but out of phase with each other by ninety degrees. The local oscillator signals and the IF signal are mixed in mixers 39 and 40 to produce two baseband signals I 43 and Q 44 that together represent the information that is of interest. They are still AC signals (even though we have "mixed them right down to DC") representing certain useful information, although they are not signals that represent that information in its most irreducible form. What is more, signals I 43 and Q 44 must be treated as an inseparable signal pair, in that both are now needed to recover that useful information.

Before passing to FIG. 1B we should note that the system architecture has thus far been described in largely functional and conceptual terms rather than as a literal description of a particular way of implementing these functions. For example, an actual system may have coarse and fine delay, and first and second intermediate frequencies, and some rather messy interactions between all these pieces. A detailed description of all that has been omitted here for the sake of brevity in exposing the central concepts that are of interest further on below.

Progressing now to FIG. 1B, the signals I 43 and Q 44 are each converted from timevariant analog signals to sequences of digital values representing corresponding instantaneous values of the analog signals. These conversions are performed by A/D converters 45 and 46, respectively. The resulting digital values (47 & 48, respectively) are stored in a memory 49.

As above, our description and explanation of the memory 49 are functional and conceptual. It will be appreciated that the input switch 50 and the output paths 51 are the result of the addressability of the memory and of the buffering of values read from the memory 49. Likewise, the memory 49 isn't really fundamentally formed of columns (52, 53, . . . 54), where each column is conveniently a stack of partitioned bins for receiving pairs of I and Q values. Instead, it is just a random access read-write memory (RAM) that has some structure imposed onto its address space by a state machine (or perhaps a microprocessor) that controls (among other things) the storage and retrieval of data into the memory 49.

It will be recalled that a "line" along a given radial might be "shot" several times before the steering is changed and a new radial chosen. There are various reasons for this, among them the desire to average out noise and, in a doppler system, to dwell on the current radial for at least two shots to gather velocity data for the different depths along that radial. If a sufficient number of shots can be made along the radial, it is possible to identify turbulent flow by rapid changes in velocity at a given location. With this in mind it will be appreciated that the various columns (52,, 53, . . . 54) are each for different (consecutive) shots along the same radial. The columns store I and Q values as pairs. The tops of the columns are for the I and Q value pairs that are of minimum depth, and the bottoms of the columns are for I and Q value pairs at maximum depth. As a pictorial device, we have drawn the figure as showing the different columns as slightly offset vertically, so that non-overlapping outputs 51 can originate from different columns but still represent the same depth; the memory itself has no such funny business.

Let there be M-many column (52, 53, . . . 54); typical values for M are in the range of, say, four to twelve. Accordingly, there are M-many output IQ value pairs 51 for each depth. These output IQ value pairs for a given depth are referred to as a "packet". The various components of a packet convey useful information. To begin with, each IQ pair is understood as legs of a right triangle enclosing the right angle. The resulting hypotenuse (averaged over the entire packet) is the (normalized for depth) amplitude of the corresponding reflected echo, is called magnitude, and will be denoted as PKT_MAG. One of the acute angles is the phase of the baseband signal represented by the analog I and Q signals, 43 and 44. Velocity for the packet is the (averaged) change in phase with respect to time (i.e., from IQ pair to IQ pair within a packet), and will be denoted as PKT_VEL. A final parameter of interest can be determined, and it is a variance that is a measure of differences between the various velocity values in the packet. A high variance can be taken as an indication of turbulence. The variance parameter will be indicated as PKT_VAR.

Refer now to FIG. 1C. The M-many outputs 51 for the current depth along the current radial are coupled to a clutter filter portion 56 of a packet processor 55. The clutter filter 56 is principally a high-pass filter that can remove certain extreme indications in the data, such as reflections from stationary objects. Following the clutter filter the data is applied to a magnitude detector 57 whose output is PKT_MAG 58, to a velocity detector 59 whose output is PKT_VEL 60, and to a variance detector 61 whose output is PKT_VAR. Regardless of what M is, there is but a single instance of each of these PKT signals for each depth. The order in which these three PKT signals (58, 60 and 62) is produced is that of increasing depth. The detectors 57, 59 and 61 could be software routines executed by a microprocessor, if it were fast enough. The preference at the present time, however, is to use dedicate high speed logic (e.g., state machines formed of PLA's) programmed specifically for these tasks. The three output values PKT_MAG 58, PKT_VEL 60 and PKT_VAR 62 are applied to a detection strength spatial filter 63. The output of the spatial filter 63 is a refined notion of velocity and variance, which when used in place of their unrefined counterparts at the input to the spatial filter 63, produce an enhanced image on the CRT 4.

The bulk of our interest from here on will be what goes on inside the detection strength spatial filter 63. To do that it will be necessary to appreciate basically what a simple spatial filter is and why it is wanted in the first place. Its fundamental component is a subsector memory, of say, four or five banks. Each bank can store an entire radial line's worth of packet magnitudes, packet velocities and packet variances. That is, those three things for all the different depths along that radial, say 512 or 1024 different depths. The different banks store consecutive radials, so that the stored data describe a contiguous sub-portion of the field of view. Hence the term "subsector memory". In brief, the subsector memory allows acquired data that is time variant (think: "is sequentially organized") along individual radials to be filtered in each of two dimensions in which the displayed image will be presented: a radial dimension and a lateral dimension. The lateral dimension is in the direction of to an adjacent radial while remaining at the same depth. Note that the acoustic echo detection mechanism is inherently a radially oriented technique, and does not of its own accord produce any time variant signals where time corresponds to the lateral dimension. Once data is in the subsector memory, however, it can be traversed along the lateral dimension to produce just such a sequentially organized sequence of signal values that can indeed be filtered, just as the time variant radial dimension signal can be filtered. This two dimensional spatial filtering appears as a smoothing of the images and a reduction in noise.

As powerful as the notion of a spatial filter is, merely having one is not the last word on image enhancement. A great deal depends upon the strategies of the filters applied to the data passing through the subsector memory. Magnitude is not generally filtered. Merely filtering velocity as an independent variable can produce a blood flow image that could still benefit from further enhancement. To provide that further enhancement we shall introduce the notion of "detection strength." Detection strength is a mapping of (magnitude, velocity) pairs representing the likelihood that the instant pair describes flow, as opposed to noise or perhaps clutter. Consider, for example, a cardiac image with doppler detection of blood flow. A low velocity and large amplitude are likely to be the wall of the heart, while a low velocity and a small amplitude are likely to be noise. High velocity and large amplitude are very likely to be blood flow, while high velocity and very small amplitude is likely to be noise. In-between are a range of possibilities, which is matched by the range of the assignable values for detection strength. By assigning a detection strength to each velocity and then sending both (along with the associated variance,too) through the spatial filter, velocities that are produced by actual flow are more likely to be correctly identified as such. The detection strength mapping may be adjusted according to the particular imaging application at hand.

To continue our overview of an ultrasound system of the type that is of interest, the filtered outputs PIX_VEL 64 and PIX_VAR 65 are applied to a scan converter 66, where the coordinate system is changed from being by depth along consecutive radials to a more convenient (X, Y) arrangement that lends itself to a raster scan display. The converted data is then stored in a frame buffer 67, after which a color map 68 allows the assignment of different colors to different values of selected kinds of data. The result is a stream of RGB signal data that is applied to the CRT 4 (along with horizontal and vertical sweeps signals, which for brevity we omit), and the subsequent formation of an image thereon.

The image may appear upon the CRT 4, although other displays and various hardcopy output devices are certainly possible. A collection of controls (not shown) allows the operator to adjust various parameters, such as gain and the filtering parameters, to obtain the most useful image.

We turn now to another topic that will be of interest. There is a mode of operation called "parallel flow" where (referring again to FIG. 1A) a given radial line is shot just as before, but twice as many receive channels are used in forming the image. The capability of doing this can be used to cut the number of transmit lines in half, while keeping the number of existing receive lines. This has the effect of nearly doubling the rate at which data is acquired and displayed. The parallel flow capability can also be used to keep the same number of transmit lines, while doubling the number of receive lines. This results in an image having greater resolution. In either use there sometimes occurs an annoying artifact called "corduroy". There follows now a brief description of how parallel flow is accomplished, and of how the corduroy artifact arises.

The starting point for understanding parallel flow is to note that if there are n-many transmit channels in use, then they are accompanied by 2n (or perhaps 3n, 4n)—many receive channels. Because of the large numbers of channels involved, practical systems currently limit n to 2. By a transmit channel we mean the transmit delay, driver and transducer involved in generating an acoustic impulse of ultrasound. For example, in FIG. 1A transmit ch. 1 would include delay 26 driver 20 and transducer 7. By a receive channel we mean the transducer, amplifiers and receive delay associated with responding to an ultrasound echo. For example, receive ch. 1 would include transducer 7, amplifiers 23 and 31 and receive delay 35. Note that transducer 7 belongs to both transmit ch. 1 and receive ch. 1. Associated with a group of receive channels is a common collection of other hardware, such as a summer, mixers and A/D converters.

To proceed by way of an example, suppose that there were sixty-four transmit channels available, and let them be denoted T1 through T64. We now require two groups of receive channels. Let these be R1 through R64 and R65 through R128. R1 through R64 are just as shown in FIG. 1A, where Ch. N is Ch. 64. Now provide a duplicate set of that same hardware, including their associated summer, mixers and A/D converters. (The extra A/D's can be supplied, or the existing ones can be multiplexed, which is cheaper.) This duplicate set has sixty-four inputs that correspond to the inputs to amplifiers 23, 24 . . . 25, and two outputs that correspond to digital values 47 and 48 (shown on FIG. 1B). (If the extra A/D's are not supplied and the existing ones are multiplexed, then the existing digital value 47 alternates between a oh. 1–64 value and a oh. 65–128 value.)

The input channels are connected in parallel in the following way: ch. 1 and ch. 64, ch. 2 and ch. 65, . . . , ch. 64 and ch. 128. The steering or focusing for the two set of channels is arranged as follows: if the transmit channels shoot a line along radial N, then one group of receive channels receives along "radial N-¼ while the other group receives along "radial N+¼. (While correct in spirit, this is a bit of a simplification. The naked truth is rather ugly, and involves complications arising from finite apertures and long wavelengths, and has been happily omitted in favor of this slight simplification.) The result is twice the number of received radials as compared to non parallel flow operation. To use this resource to provide improved resolution, the incremental angle between received radials is cut in half, thus providing twice the number of radials for the same field of view. The data from the two groups of channels goes into the memory in the obvious way; as consecutive radials interleaved to be in their correct order.

The problem arises when the two groups of receive channels do not have exactly the same gain. True, they can be matched to a point, typically to within a db or so, on average. But it must be remembered that the groups would have to track gains not only laterally, but for all depths, too. Peak gain variations might be a few db at certain places in the image. Now, there is of necessity a thresholding process which blanks to black any data that is deemed too weak or too noisy to display. This means that it is possible for one group of channels to produce for consecutive radials data that for a range of consecutive depths is above the threshold while the other group does not, solely because the gain difference produces data that straddles the threshold. When this happens, the display possesses, at that range of depth and for those radials, a radial-by radial picket fence like quality which is what we have termed "corduroy". That term is used because it suggests a striped quality in the display. To complete the picket fence analogy, the pickets would be normally colored radial regions for the detected velocity, while the space between the pickets (intervening radials belonging to the other signal path having the lower gain) would be black. The height of the pickets might be, for example, in the range of from five to twenty-five percent of the length of a radial, and could exist laterally for a large number of consecutive radials; accordingly, the effect can be quite annoying.

SUMMARY OF THE INVENTION

An imaging system where a location in the image has associated with it two parameters measured in a noisy environment, such as reflection amplitude and doppler shift (velocity) in an ultrasound system, can assign a detection strength to each location. Detection strength is a mapping from each possible combination of the two parameters into a scalar value that represents the likelihood that one of the measured parameters is not an artifact of the noise in the environment. The detection strength values can be filtered and then used to determine whether to accept or reject the measured parameter. In particular, the detection strength signal can be spatially filtered by storing its sequence of values in a memory for all or a portion of the image. Spatial filtering involves filtering sequences of values obtained by traversing along different axes in the data.

Since detection strength, especially when filtered, can be used to decide whether to accept or reject a measured parameter, a more generous or optimistic filtering strategy for that measured parameter is permissible; relying upon a filtered detection strength to trim away suspicious regions in the image. This combination of filtering allows better filling of holes in the image and improved smoothing of the edges of the image.

The filtered detection strength signal can be used to compensate for unwanted side effects of other filtering done during the processing of the measured parameters. For example, a clutter filter in a cardiac ultrasound system also attenuates innocent velocity signals for low velocities. The effect of this attenuation can be compensated by the detection strength mapping. (As will be seen, we adjust the effect; we don't "un-attenuate" the data.)

The measured parameters themselves are generally filtered. Digitizing a time variant signal produces a sequence of digital values. When some number of consecutive such digital values are retained they may be applied as an address to a ROM whose output value represents a filtering of the input values. When the number of input bits exceeds the address space of the ROM the input values can be bifurcated into MSB's and LSB's, with the MSB's applied to the ROM as the address. The LSB's are sent to a MUX. The output value produced by each input combination can include two fields, one of which is the filtered or transformed value of the applied MSB's, and the other of which is a selector field. The selector field can be pre-encoded to direct the MUX to select the LSB's that ought to be associated with the filtered or transformed value produced by the ROM in the other field. These recovered LSB's are then conjoined or otherwise used with that filtered or transformed value.

The corduroy artifact of parallel flow operation can be removed by incorporating into the lateral detection strength filter a weighting scheme wherein the sum of the weights for the odd numbered radials in the filter's aperture equals the sum of the weights for the even numbered radials in the filter's aperture.

BRIEF DESCRIPTION OF THE DRAWINGS

FIG. 6 is a block diagram describing a median radial velocity filter having a ROM addressed by fewer than the number of bits supplied in the input data to be filtered, and incorporating an LSB recovery mechanism to disguise that fact.

DESCRIPTION OF A PREFERRED EMBODIMENT

Figure 2:
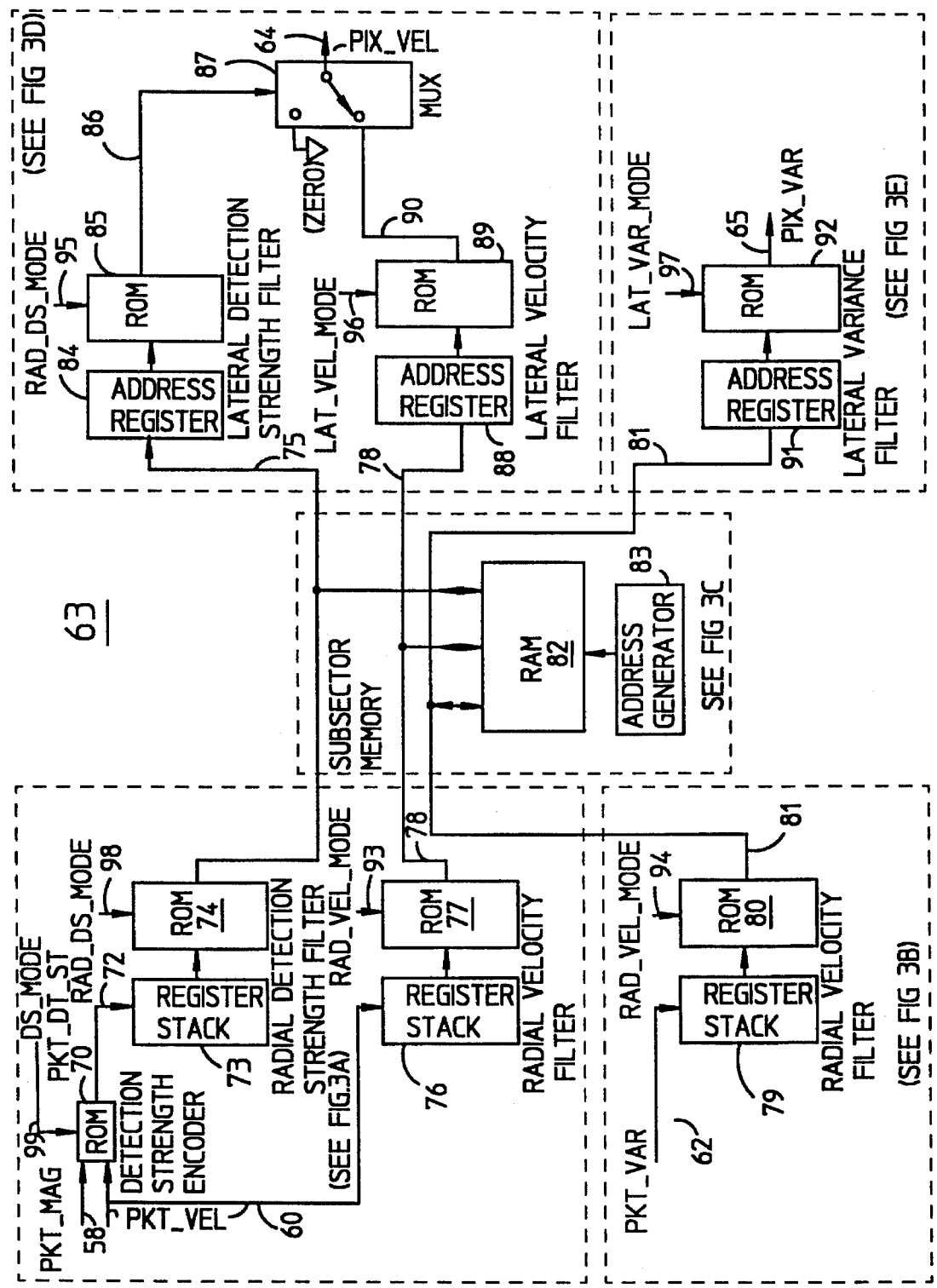
FIG. 2 is a very simplified block diagram of the detection strength spatial filter of FIG. 1C, and also serves as figure map tier FIGS. 3A-E.

Refer now to FIG. 2, which is a very simplified block diagram of the detection strength spatial filter 63. This figure serves two purposes: First, it gives an idea of the structure of the data flow into and out of the spatial filter 63, so that one is less likely to get lost in the more detailed FIGS. 3A-E which cover the same material; and second, it serves as a figure map for the spatial relationship between the various portions of FIGS. 3A-E.

Figure 3A:
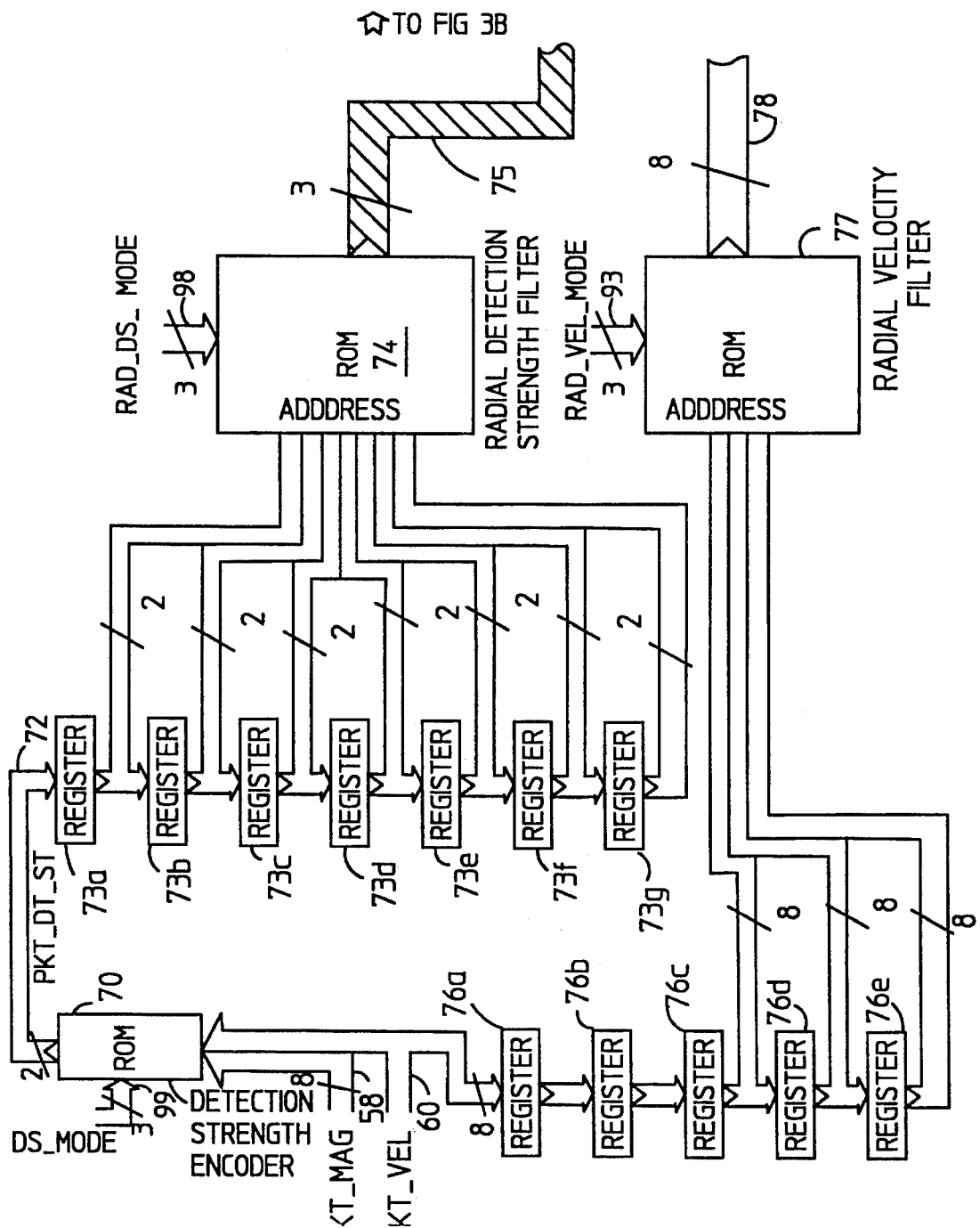
FIGS. 3A-E are a detailed block diagram of the detection strength spatial filter depicted in FIG. 1C.
Figure 3B:
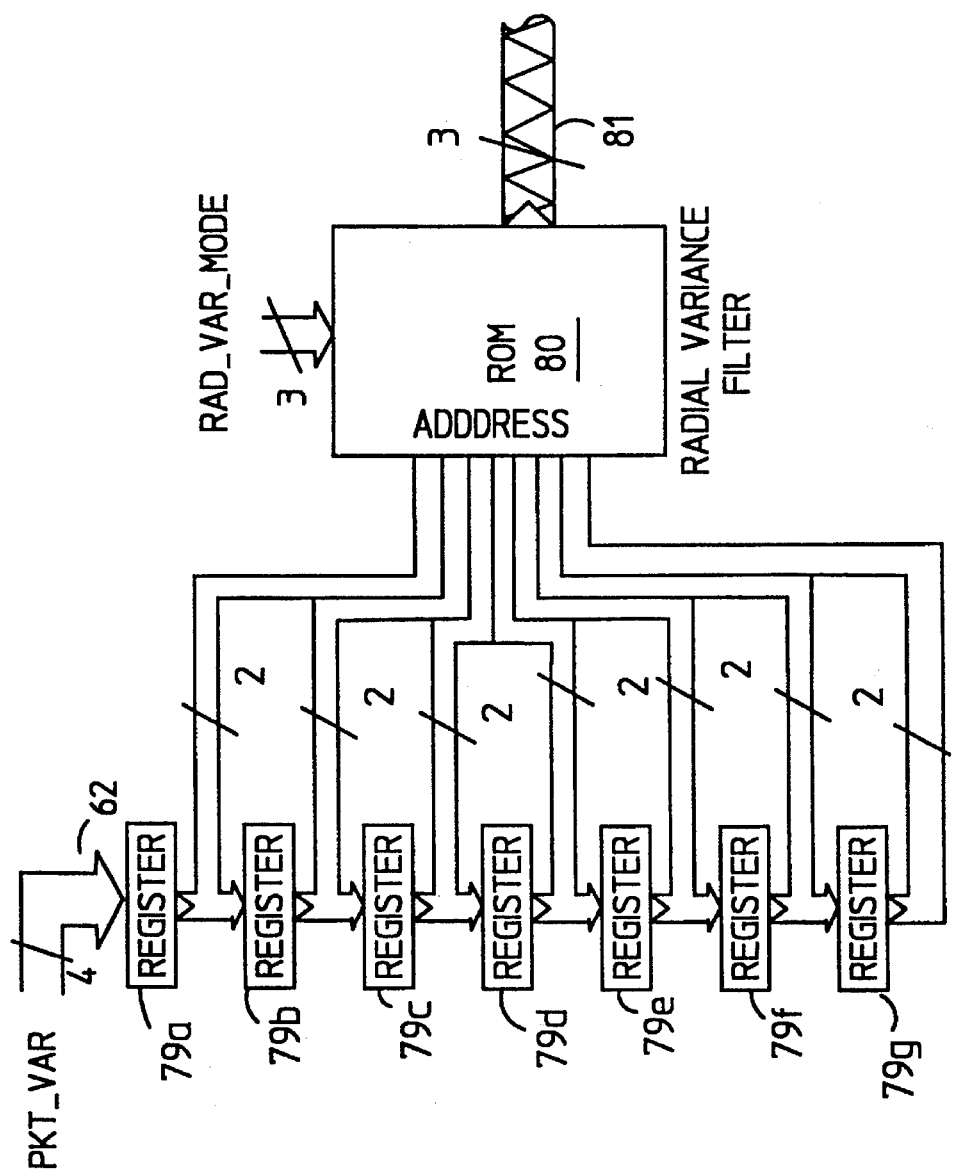
Figure 3C:
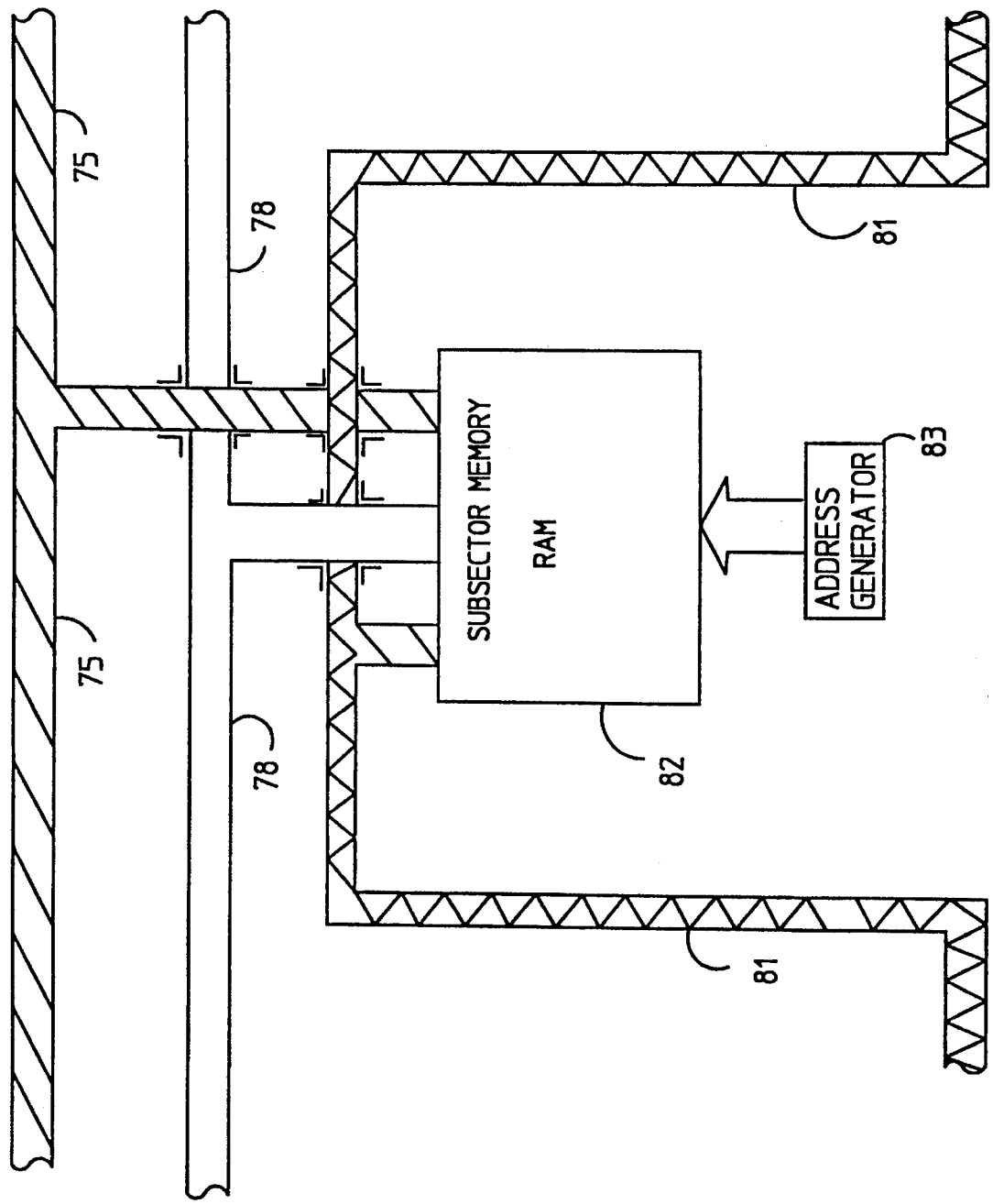

Consider first the upper left-hand portion of FIG. 2, corresponding to FIG. 3A. Observe that PKT_MAG 58 and PKT_VEL 60 are applied to a ROM 70 that functions as a detection strength encoder. Detection strength may be any useful function of the two variables magnitude and velocity. The current values for PKT_MAG and PKT_VEL are applied as an address to the ROM 70; the contents of the addressed location are the value of the function. ROM 70 is thus a look-up table. It is actually several look-up tables representing different useful encodings; the signal DS_MODE 99 provides additional most significant address bits to select which overall portion of the ROM's address space the velocity and magnitude are used to address. That is, the signal DS_MODE allows the selection of different mappings for detection strength to be used by the detection strength encoder ROM 70. The mapping may change according to the depth along the current radial or it may change by overall application. The output of the ROM 70 is a multi-bit value called PKT_DT_ST 72.

As new pairs of PKT_MAG 58 and PKT_VEL 60 are produced for deeper locations along the current radial a corresponding value of PKT_DT_ST 72 is also produced. Thus, for each radial there is a sequence of PKT_DT_ST values. These are sent to a register stack 73 where the last several values in the sequence are retained to form an address that is applied to a look-up ROM 74 that operates as a radial detection strength filter. This ROM filters variations in the detection strength 72 in the direction of depth along the radial line. The preferred filter strategy is one of weighted traveling average. Several different filters may be encoded within the ROM 74, and the one used is selected according to the value of the signal RAD_DS_MODE 98. The output of the radial detection strength filter (ROM 74) is a multi-bit value 75 that is at various times stored in either the address register 84 or in the subsector memory 82.

The sequence of values that occurs for PKT_VEL 60 goes not only to the detection strength encoder ROM 70 but also to a register stack 76. Register stack 76 retains the last several values in the sequence, and they form an address applied to a ROM 77 that functions as a radial velocity filter. The value of RAD_VEL_MODE 93 provides the MSB's of the address, and thus select one of several filters encoded in the ROM 77. The output of the radial velocity filter (ROM 77) is a multi-bit value 78 that is at various times stored in either the address register 88 or in the subsector memory 82.

In a similar fashion the sequence of values that occurs for PKT_VAR 62 goes to a register stack 79. Register stack 79 retains the last several values in the sequence, and they form an address applied to a ROM 80 that functions as a radial variance filter. The value of RAD_VAR_MODE 94 provides the MSB's of the address, and thus select one of several filters encoded in the ROM 80. The output of the radial variance filter (ROM 80) is a multi-bit value 81 that is at various times stored in either the address register 91 or in the subsector memory 82.

The subsector memory, in conjunction with the storage afforded by the address registers 84, 88 and 91, provides the storage necessary to filter in the lateral direction; that is, over some number of consecutive radials and at each depth. Whereas filtering in the radial direction can be accomplished as the data for the consecutive depths along a radial arrive (it is only necessary to store the last several values along the same radial), to filter in the lateral direction over, say, five radials, and at the, say, two hundredth and third depth, one has to store all of the data for each of the preceding four radials, and then as the data for the next two hundredth and third depth was coming in (and let's name it Rnew@D203) all five consecutive two hundredth and third depths for the last five radials would be available. As with the radial filters, these values are conjoined to form an address applied to a ROM that functions as a look-up table that implements the filter.

Now, it will easily be appreciated that we are not finished with Rnew@D203 when Rnew@D204 comes in. However, we can't just shift Rnew@D203 over and keep it as part of the address applied to the ROM. Instead, we have to store it for future use, since at the moment we are interested only in values belonging to Rxxx@D204, of which we want five: Rnew, Rnew-1, Rnew-2, Rnew-3 and Rnew-4. Hence we store Rnew@D203 in the subsector memory 82 at a location associated with Rnew-1@D203, since by the next time we need that value it won't be as part of the latest radial (Rnew), but as part of the previous radial (Rnew-1). So each time a new value (that is, for each of detection strength, velocity and variance) is available it is placed in the associated address register (and eventually into the RAM 82 that is the subsector memory). Also, the previous other four values for that parameter at that depth are retrieved and sent to the address register associated with that parameter. Once the oldest value reaches the address register it will no longer be needed, and its location in the subsector memory can be taken by the newest value. That is, in the subsector memory Rnew replaces Rnew-4, and we simply keep track of which memory locations correspond to these constructs as more data comes in; the location of Rnew might be said to be a "revolving" location. Upon reflection, it will be appreciated that the RAM 82 can be construed as having four banks, where each bank holds the data (by depth) for an entire radial. As new data comes in, the bank holding the data for the oldest radial is being overwritten with the data for the newest radial. Them is a lot of addressing going on for the subsector memory. The address generator 83 is preferably a high speed state machine, although it is possible that a microprocessor could be used as well.

A special case occurs at the beginning of each frame. (A frame is the shooting of all the radials within the field of view.) As will become clear, the various filters have center locations within a filter aperture (not to be confused with the aperture for the probe), and they must coincide. Furthermore, filtering cannot actually start until the filter's aperture is filled with data. As a consequence, the field of view that is produced from the filtering operation is slightly less in size (by a few locations at each end of both the radial and lateral dimensions) than the field that was actually shot. That can't be helped; it comes with the filtering. The solution would seem to be the shooting of extra lines to prevent diminishing the lateral extent of the displayed image. However, there is the extra time required to shoot those extra lines, and that extra time can produce an unwanted decrease in the update rate at which new data can be put into the frame buffer 67. It turns out that the update rate is under certain circumstances already lower than desirable, even without the extra wide filter aperture desired for the spatial filtering of detection strength values. What to do?

The solution is to not shoot the needed extra lines, and simply pre-load the registers and subsector memory with zeros, as if those zeros had been legitimately produced by actually shooting the lines. This can be done very quickly, thus avoiding the time penalty. Other values might be used in place of zero, but zero is preferred since it doesn't introduce severe color artifacts and its effect is readily smoothed out by the spatial filter. The present system performs this pre-load for the "phantom" radials at the start of the filed of view, but owing to the absence of an end-of-field-of-view signal within the spatial filter assembly, (there is such a signal in the system, but no provision was made to supply it to places where no need was felt at that time, which was well before the present detection strength spatial filter was invented) the last two "extra" radials really do get shot, rather than pre-loaded as phantom radials. Ideally, there would be pre-loaded phantom radials at each end of the field of view.

To conclude our discussion of FIG. 2, observe now the three lateral filter ROM's 85, 89 and 92. Each is addressed by the contents of an associated address register (84, 88 and 91), each of which really comprises several registers. The filtering strategy of each lateral filter can be changed, just as with the radial filters, by the various signals LAT_DS_

MODE 92, LAT_VEL_MODE 96 and LAT_VAR_ MODE 97. The output of the ROM 85 that functions as the lateral detection strength filter is a single-bit value 86 that can be used as a confidence/no confidence indicator for the velocity. The preferred filter strategy for the lateral detection strength filter is one of a weighted traveling average. The velocity (now filtered radially and laterally) is a multi-bit value 90 produced by the ROM 89 that functions as the lateral velocity filter.

We should dwell for a moment on the lateral detection strength filter ROM 85. Now, it is not difficult to characterize the radial detection strength filter ROM 74 as a filter: a collection of detection strengths go in, and a detection strength comes out. Over time we expect to observe smoothing, or whatever transformation is performed by the filter, and we do. It is a traveling average type of transformation. In contrast, however, a collection of detection strengths is applied to the lateral detection strength filter and a one-bit go/no-go "confidence indicator" signal comes out. Yet we also said that it, too, was a traveling average mechanism. And indeed it is, but with a threshold detection rule applied to the result of the filtering. The level of the threshold is one of the things that can be set by different values for LAT_DS_MODE 95.

The velocity value 90 and another fixed value representing a velocity of zero are coupled to a MUX 87, where the single-bit doubly filtered detection strength value 86 is used to select which is sent forward as PIX_VEL 64. If there is confidence in the velocity value 90 from ROM 89 then it is selected by MUX 87, otherwise the value of zero is selected.

Refer now to FIGS. 3A–E, which are a more detailed version of the material depicted in FIG. 2. While it is not necessary to completely describe FIGS. 3A–E from the beginning, it is well to point out certain things of particular interest.

To begin with, note that register stacks 73, 76 and 79, as well as address registers 84, 88 and 91 have been expanded to show how they operate. The register stacks operate as "push only, drop out the bottom" structures whose internal contents are available for use. They may also be thought of as shift registers whose shift operation relocates entire words at a time instead of a bit at a time. Although it is not shown, the register stacks are clocked by a signal that corresponds to digitizing the next depth along the current radial. The address registers, on the other hand, are individually addressable, and have their contents written thereto as needed.

An interesting feature of those structures concerns the operation of the various filters comprising the detection strength spatial filter 63. All of the individual filters need to be filtering around the same location in the image (i.e., along the same radial and at the same depth), which location we shall call the center location. However, in the particular spatial filter 63 not all of the filters have the same size filter aperture, or span. The radial and lateral velocity filters span three locations: one on either side of the center location. The radial detection strength filter, on the other hand, has a span of seven, which is three on either side of the center location. The lateral detection strength filter has a span of five, or two on either side of the center location. One way to visualize this process is to imagine a rectangular array of locations seven on a side and five locations wide; it has a center location right in the middle of the rectangle, since there are an odd number of locations per side. This rectangle of thirty-five locations represents a region about each location in which detection strength is filtered in both directions. Superimposed upon this seven by five rectangle is a smaller three by three square, whose center location coincides with the center of the seven by five rectangle. This square of nine locations represents the region within which velocity is filtered in each direction. The co-located center locations of the two spatial filters traverse the image by traveling down a radial, then down the next radial, and so on. However, the filters have to wait until enough radials have been completed, and then they lag behind the newest radial by the number of locations (two) from the center to the edge of the largest (in the lateral direction) of the square and the rectangle.

Upon reflection it will be appreciated that registers 76a and 76b for the radial velocity filter are needed to correspond to registers 73a and 73b for the radial detection strength filter, even though their contents are not used other than for data retention. The data retention is absolutely necessary, since that data will eventually be used as part of the three location span of the radial velocity filter, and must therefor be saved at the time it occurs, so that it may be eventually shifted into place as newer data is saved. Accordingly, it can be seen that registers 76d and 73d each contain center locations. On the lateral side, however, the storage function is accomplished by the RAM 82 of the subsector memory. Thus registers 84c, 88b and 91c contain the center locations, and do indeed correspond to registers 73d, 76d and 79d, respectively.

Although it is not shown, the value of PKT_MAG 58 applied as one input to the detection strength encoder ROM 70 is a compressed eight bit value representing an original value expressed by a much larger number of bits (the sum of all the ten-bit magnitudes within the packet).

Notice also the signal DS_MODE 99, which is a three bit value usable to vary the nature of the detection strength mapping used upon the combined sixteen bits of PKT_MAG and PKT_VEL. Together, this amounts to nineteen bits of addressability, which at the present time is a fair chunk of address space. It would be advantageous if DS_MODE could be wider, say, six or eight bits. Then one field of DS_MODE could represent application information that would affect the overall type of mapping for detection strength, and another field could represent at least a coarse indication of depth.

Figure 1A:
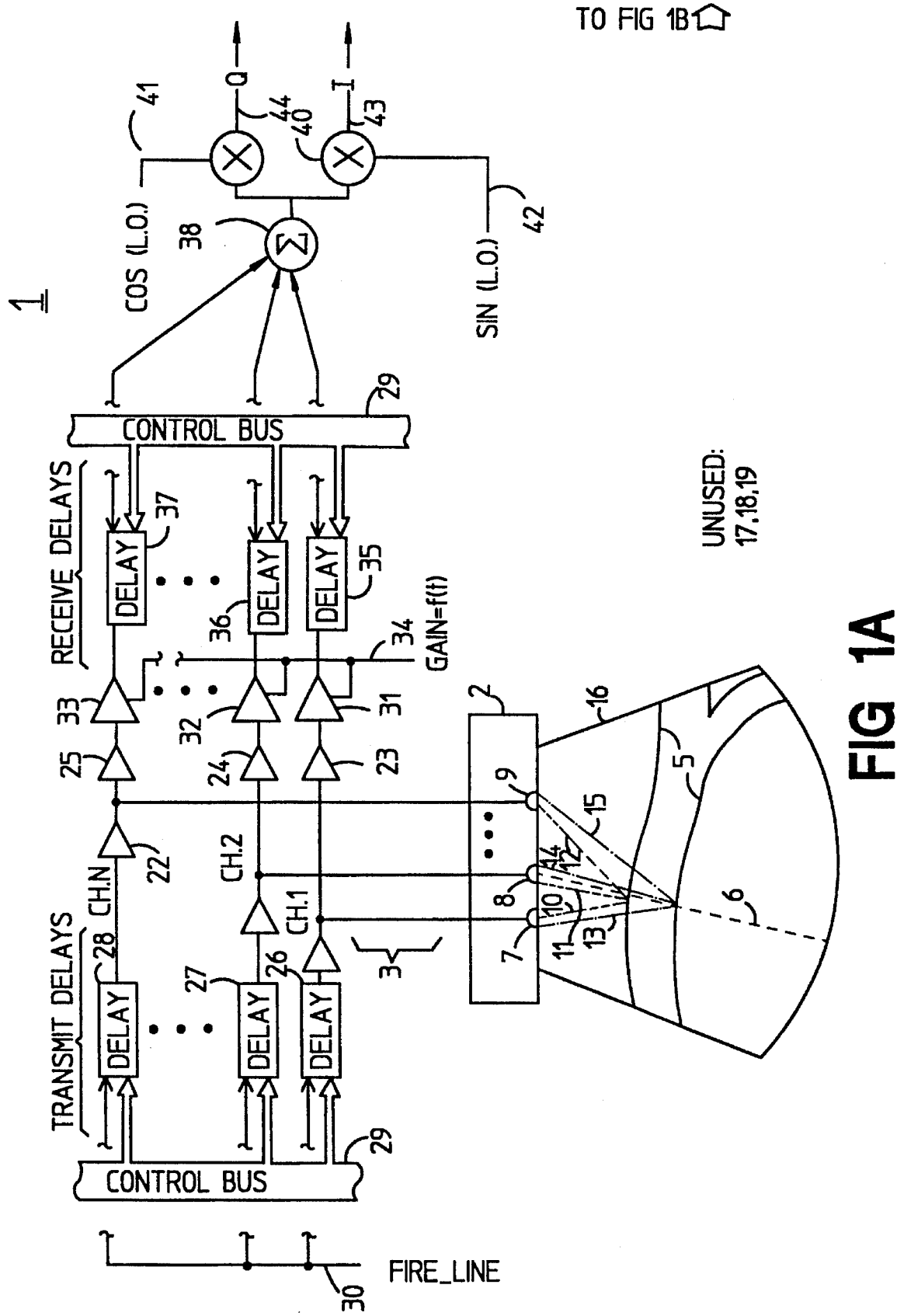
FIGS. 1A-C are a simplified block diagram illustrating the use of an ultrasound system to form an image of a organ within a body.
Figure 1B:
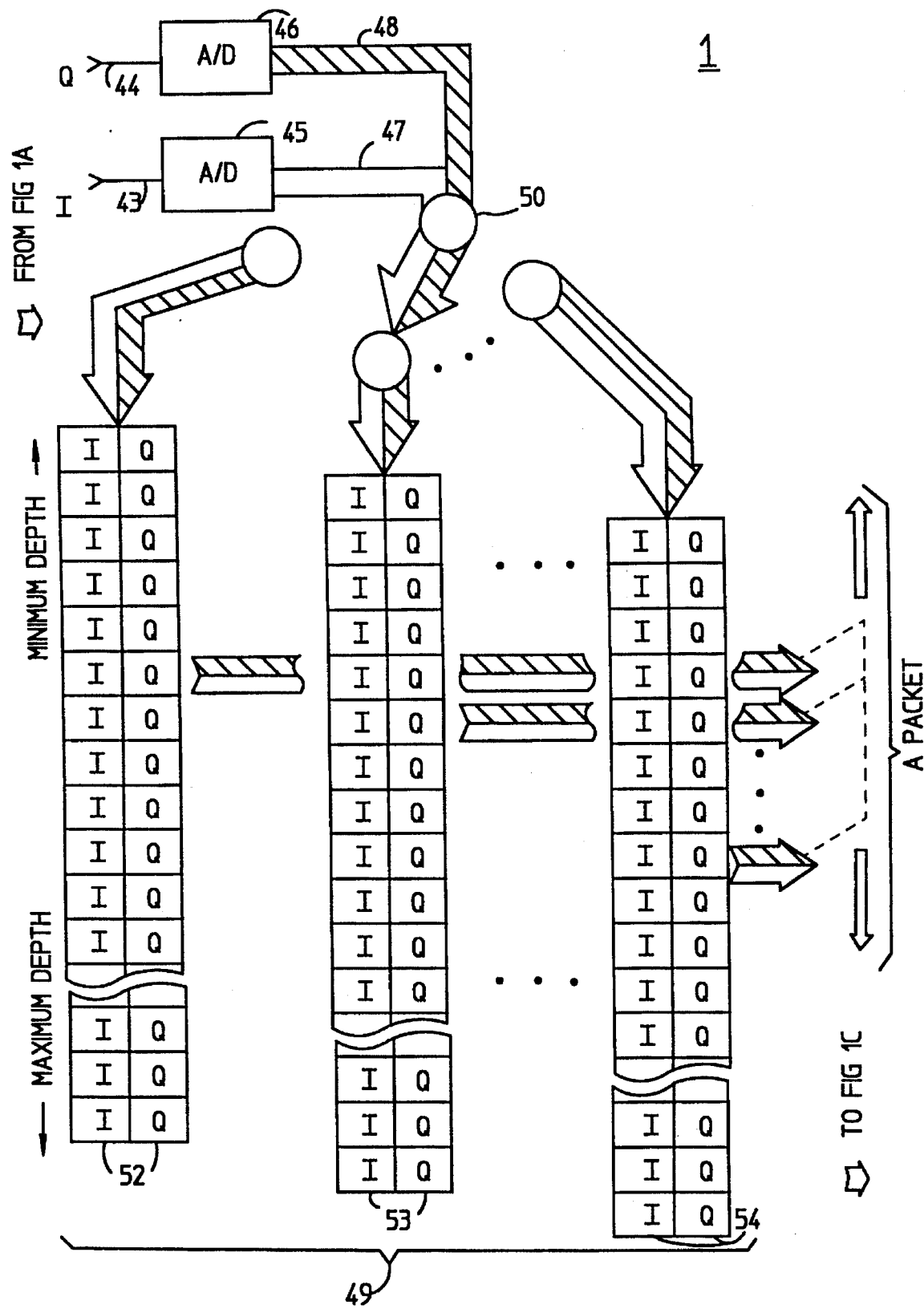
Figure 1C:
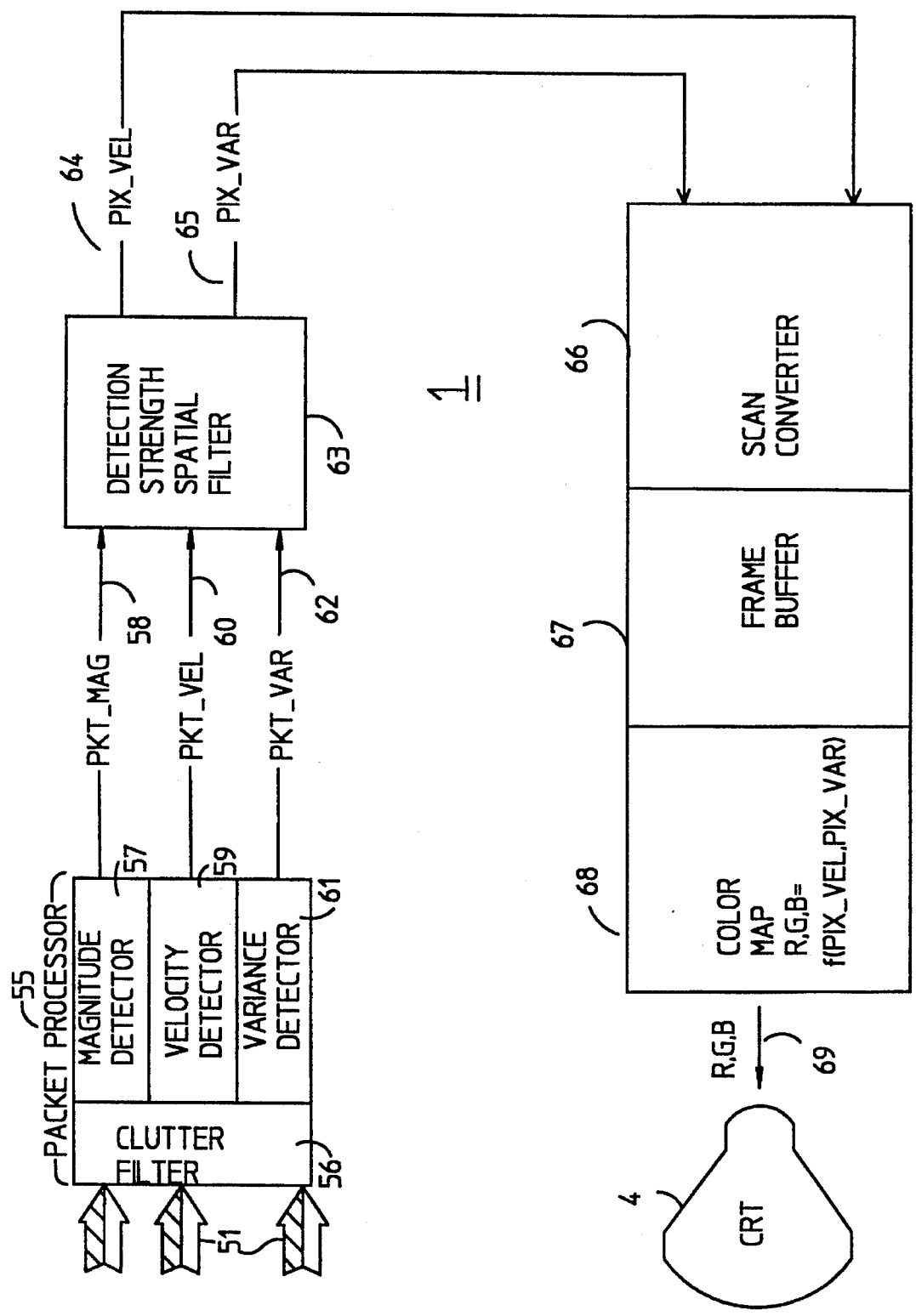

Depth indication provided to the detection strength encoder ROM 70 would be useful for the following reason. Recall that the gain of amplifiers 31, 32 . . . 33 (see FIG. 1A) was increased over time to compensate for round trip attenuation owing to increasing depth. Recall also that there is a limit on this gain increase, owing to the noise floor and eventual deterioration of the signal to noise ratio beyond a point which is acceptable. It is when this gradual deterioration exceeds acceptable limits that depth sensitive mappings for the detection strength encoder ROM 70 would be of value.

Presently available ROM's do not have an address space large enough for all these uses to occur at once within a single ROM. One solution to this problem would be to have banks of detection strength encoding ROM's, with each addressed by the same values, but with a multiplexing arrangement to select which ROM's output is allowed to feed registers 73a–g. Of the two parameters application type and depth, one is part of the address applied to all of the ROM's, while the other drives the selection multiplexer.

Figure 3D:
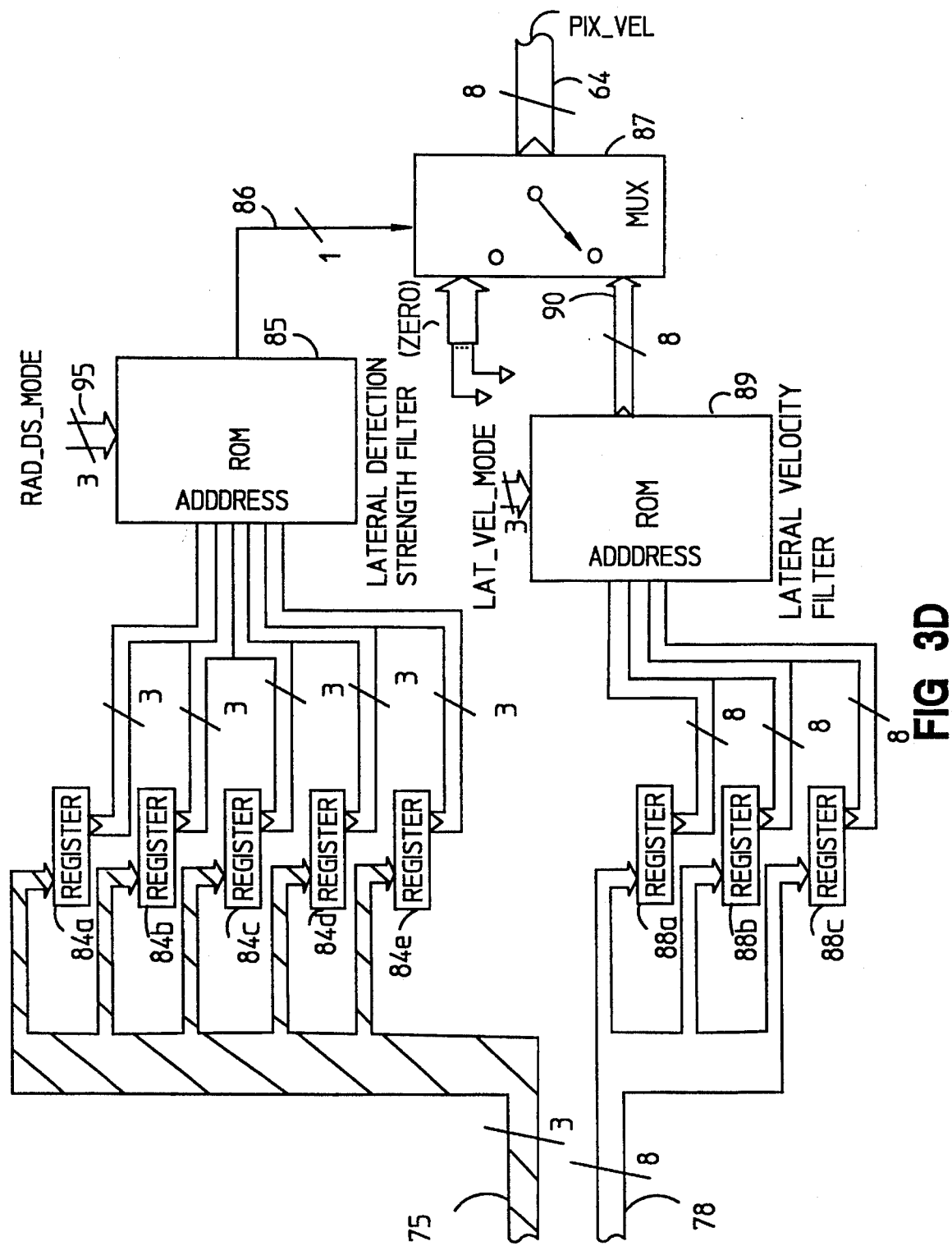
Figure 3E:
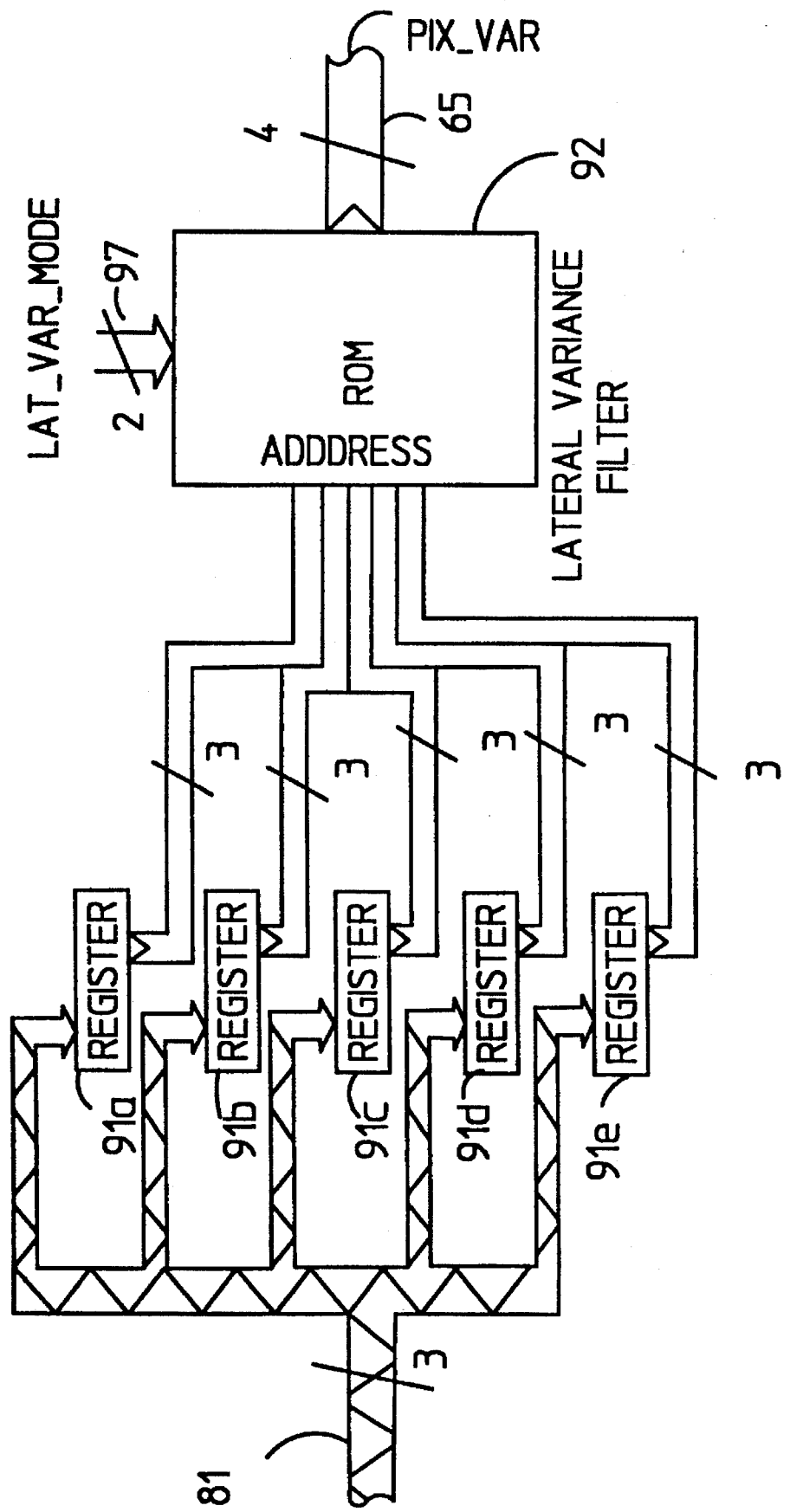

Refer now to FIG. 3D, and observe how the one-bit output from the lateral detection strength filter is applied to MUX 87 to select whether the spatially filtered velocity 90 becomes PIX_VEL 64 or PIX_VEL 64 is forced to have a value of zero. Values of zero are mapped into black in the displayed image. Regions interior to an image that are black may be holes that in an ideal setting would not be black. (In some images, however, black might be the right answer, in which case the interior black region would not be a hole, but a legitimate representation of an actual feature, such a bifurcation in flow.) We have several further observations pertinent to this part of the detection strength spatial filter 63, which suppresses velocities having an inadequate spatially filtered detection strength. Notice the signal LAT_DS_MODE 95. This corresponds to the signal RAD_DS_MODE 98 of FIG. 3A. These signals are used to control the type of filtering performed upon the detection strength values, and should not be confused with DS_MODE 99, which affects the detection strength mapping that produces the values to be filtered. The signals LAT_DS_MODE 95 and RAD_DS_MODE 98 should be selected and changed together.

By forcing PIX_VEL 64 to have a value of zero when the spatially filtered detection strength is inadequate, ragged edges around an image are smoothed. Because the velocity filtering is spatial filtering (and is more optimistic, or generous), there is a much better chance that holes will be filled in with the surrounding color.

One might ask why the signal PIX_VAR 65 is allowed to proceed unaltered while PIX_VEL is forced to zero. That is, why allow a region to be classified as turbulent when the spatially filtered detection strength is inadequate. Should PIX_VAR 65 not also be forced to a value connoting that it is not valid? Should not there be a MUX for the output 65 of the lateral variance filter ROM 92? The answer is that there could be, but that in the present system it is not necessary because the corresponding function is performed (downstream) in the color map 68. The color map 68 suppresses the variance for locations that have a velocity of zero.

Figure 4:
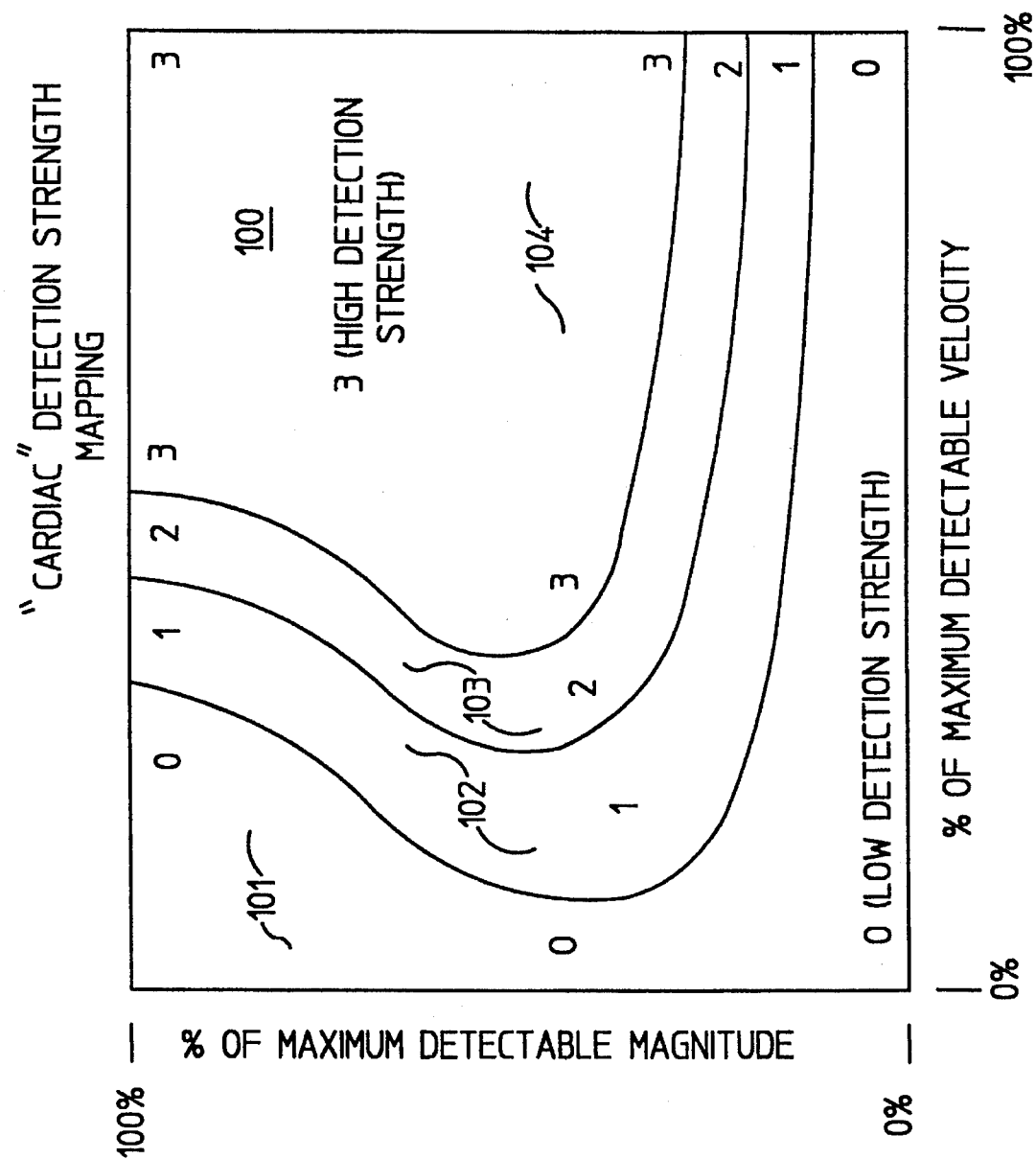
FIG. 4 is a graph describing a cardiac detection strength mapping for a detection strength encoder ROM of FIGS. 2 and 3A.

A further appreciation of the notion of detection strength may be gained from a study of FIG. 4, which is a representation of one preferred way in which the detection strength encoder ROM 70 can produce the signal PKT_DT_ST 72 in response to the application of the signals PKT_MAG 58 and PKT_VEL 60. As previously explained, the ROM 70 treats the combined input values as a unique combination; the conjoined values simply form an address. At that address is encoded the appropriate detection strength for the type of application at hand. In the present embodiment the ROM 70 outputs two bits, which encode four different detection strengths: 0, 1, 2 and 3. These are the regions 101, 102, 103 and 104, respectively. The value 0 is the weakest, while 3 is the strongest. FIG. 4 shows the general arrangement of what detection strengths are produced for different combinations of input variables. The two variables are, of course, magnitude and (absolute value of the) velocity, and the ordinate and abscissa are respectively the percentage of the maximum detectable values of those variables.

FIG. 4 depicts a detection strength mapping 100 suitable for use in a cardiac application where high velocities are assigned high detection strengths unless they have very low magnitudes. Also, low velocities are assigned low detection strengths, regardless of the magnitude. Once again, consider a cardiac image with doppler detection of blood flow. A low velocity and large amplitude are likely to be the wall of the heart, while a low velocity and a small amplitude are likely to be noise. High velocity and large amplitude are very likely to be blood flow, while high velocity and very small amplitude is likely to be noise. In-between are a range of possibilities, which is matched by the different assignable values for detection strength between 0 and 3.

Figure 5:
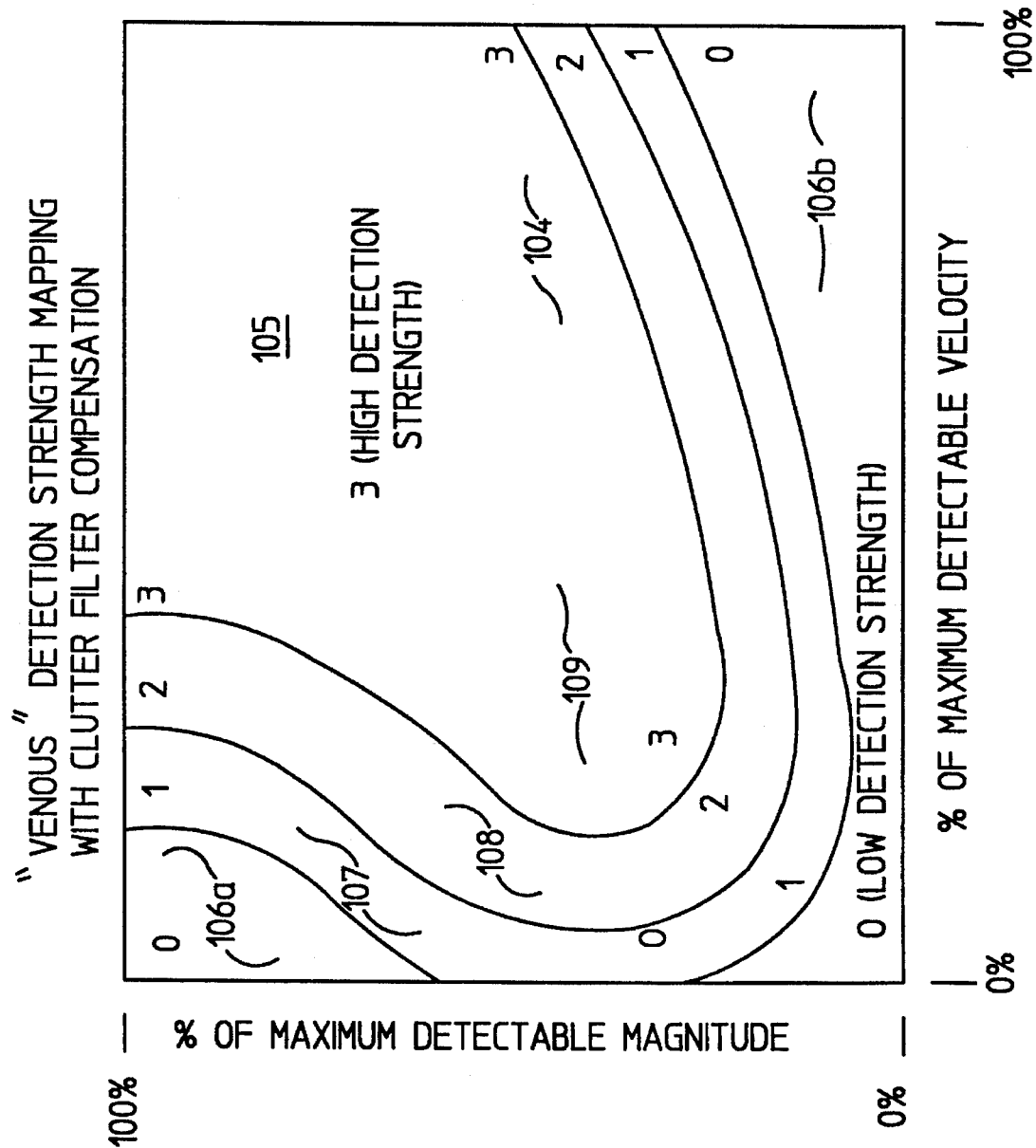
FIG. 5 is a graph describing a venous detection strength mapping for a detection strength encoder ROM of FIGS. 2 and 3A.

FIG. 5 is a graph of detection strength mapping 105 similar to that of FIG. 4, except that it has a different shape that is more suited to venous blood flow and clutter filter compensation. In comparison with FIG. 4, low velocities receive more favorable treatment so long as there is at least some minimum magnitude, although low velocity with very high magnitude is suspect (as tissue motion) and rated is accordingly. Concerning the clutter filter compensation, recall that the clutter filter is essentially a high pass filter in the processing of the doppler signal. Low velocity signals are necessarily attenuated by the clutter filter, even those that might indeed represent flow. This attenuation can be offset by giving selected combinations of flow and magnitude favorable values of detection strength. This can be done with almost as sharp a knee as desired. (The encoder ROM 70 is just a look-up table, after all, and is free of any such construct as a time constant. Observe how regions 106a and 106b intersect the ordinate.) As a result, the main effect of the clutter filter can be retained while the unwanted artifact produced by its slope (attenuation of innocent low velocities) is compensated for.

The effect of the signal DS_MODE 99 may be understood by a general appreciation that the particular spacing between detection strength regions (101–104 and 106–109), the severity of the inflections in the boundaries therebetween, and, the locations of those boundaries, may be changed to produce a family of related mappings.

Finally, it should be noted in connection with FIGS. 4 and 5 that mapping produced by the detection strength encoder ROM 70 can be arbitrary. It could resemble one of the ones shown here, where there are no regions completely enclosed by a boundary with another region. Or, it could look like a contour map, where regions are enclosed by boundaries that may touch but do not cross. And lastly, although it is hard to imagine an application, the mapping could, either in places or in its entirety, be so discontinuous that no meandering boundary lines can be drawn. In such a case each combination of the discretely quantized input variables would represent its own region, and would be depicted as a point.

To further appreciate how a detection strength filter can be employed, it is useful to understand how it might be desirable (as it is in the preferred embodiment described herein) to adjust the other filters in the system. In particular, we are interested in this case (doppler detected blood flow) in the radial and lateral. velocity filters. As a starting point, it is useful to think of the overall detection strength filtering strategy this way: The velocity filters should tend to include as candidates just about any velocities that are not zero. In fact, they should try to avoid an output of zero unless there is no other rational choice. This has the effect of tending to fill in holes and propagating ragged edges outward (it doesn't necessarily smooth them, although it might). Then the filtered detection strength is used to trim away those values that are suspicious. Conventional radial and lateral velocity filters are too stingy, and must be made somewhat more generous, or optimistic.

The usual velocity filter is a median selector. (An odd number of inputs are put into a list ordered by value. The entry with an equal number of entries above and below is the selected value.) This is a very good strategy for eliminating noise, as it tends to amputate the "bad" values without contaminating the "good" values through averaging. However, it has an unfortunate fondness for putting out zero in a noisy stream of data hovering around zero. Hence, in the preferred radial and lateral velocity filters used with the spatial detection strength filter the median filter strategy is modified to try to avoid zero as an output. This is done by replacing a selected value of zero by another value if there is a nonzero value in the data. Here is the zero replacement rule: if there is only one non-zero value in the data set, then choose it. If there are two non-zero values, and one is positive and one is negative, then measure the distance from the negative value to minus one half of full scale and measure the distance from the positive point to plus one half of full scale. The point that has the smallest distance is chosen. A variation of this is to treat any nearly zero value as if it were zero, and proceed as before.

This process may be thought of as propagating the edge of a velocity region outward at a boundary, or inward toward a hole. The extended, or enlarged region is now subject to "trimming" according to the spatially filtered detection strength.

Another way to adjust the radial and lateral velocity filters would be to dispense with the median strategy altogether, and replace it with some sort of peak detection, perhaps coupled with a decay time constant.

Another topic concerning the velocity filters is of interest. Refer to FIG. 6 and note that it is an expanded depiction of the radial velocity filter 77 in particular, and by implication, of the lateral velocity filter 89 as well (the various signal names would need to be changed in the obvious way). A number of multi-bit input values (111,112, 113) are presented to a ROM 110 which is to act as a filter, producing an output value 113. Unfortunately, the number of bits (including a mode selection value 120) exceeds the address space of a single ROM. What to do?

The solution is to first, restrict the filtering strategy to one of selection of a median value (as opposed to, say, true averaging of the complete input values). Second, a number of least significant bits (LSB's 117, 118, 119) of each input value is separated from their associated most significant bits (MSB's 114, 115, 116). The MSB's 114, 115 and 116 are applied as an address to the ROM 110. They represent the "rounded" input values, which are for convenience termed "A", "B" and "C". The contents of the ROM 110 are programmed in a known way to select the median value of "A", "B" or "C" as if they were the actual complete values in the first instance. That is, the output 113 produced from the ROM 110 is the median of "A", "B" or "C", and thus is exactly one of "A", "B" or "C" with their same number of bits.

Meanwhile, the three sets of LSB's 117, 118 and 119 are applied as inputs to a MUX 112. Its output 114 will be exactly one of those sets, according to the value of an LSB selector value 121 also applied to MUX 112 and produced by the ROM 110. The recovered LSB's 114 are conjoined with output 113 to produce a complete median value 122 that is identical, bit for bit, with the value of one of the applied input values 111, 112 and 113.

Here is how to appreciate why the LSB selector value 121 can direct MUX 112 to recover the correct collection of LSB's. Keep in mind that it is well known how to put the median selection property into the ROM 110. We needn't delve into how that is done to appreciate the LSB selector value. Instead, note that the ROM 110 does not "pass" a selected value, as say, a MUX does. Rather, it "re-creates" from its own internal bit patterns the value to be output. Now, simply consider that the value to be output is made slightly wider than is necessary to represent that value (the extra bits are the LSB selector value 121). The amount of the increase is the number of bits needed to indicate how many different inputs are being selected from to produce the output. In the figure, three different inputs (114, 115, and 116) are applied, so two extra bits will suffice. So, if the value that is "A" is to be produced on output 113, the LSB selector value designating addressing bit segment "A" for the MUX 112 is what appears at output 121 of the ROM 110. The key is to remember that at the time the bit pattern within the ROM is chosen it is known which input address section (114, 115, 116) will have a value that matches the output value to be produced on 113. So it is simply a matter of encoding that information in the extra LSB selector field for each combination of values for "A", "B" and "C".

Upon reflection, it will be appreciated that this LSB recovery mechanism may require that the ROM 110 implement a look-up strategy that is one of selecting one of the input addressing segments "A", "B" and "C" as the value of the output. Most true averaging techniques are probably ruled out, since there is no guarantee that any of the LSB segments 117, 118 and 119 is the average of those LSB's.

There is also one limitation, or exceptional situation, that one ought to be aware of. There are circumstances where the circuit of FIG. 6 does not produce the correct median value. Suppose MSB's 114, 115 and 116 are identical. In such a case the selection ought to be made according to the LSB's, but of course, will not be. The selection in such a case has to be arbitrarily encoded in advance. Fortunately, the error is "small", in that its value is limited to just the range of the LSB's. Note, however, that the occurrence of this circumstance can be indicated by an otherwise unused value of the LSB selector bits 121, so that if need be, some further action can be taken.

There is one other interesting possibility involving extra values of the LSB selector bits 121 that warrants attention. It may be that some special combination of input values ought to produce a special output. Suppose, for example, that the inputs fit a certain pattern around zero. It may be desirable to suppress the normal median selection in favor of forcing the entire output 122 to be zero. This can be arranged by signalling the occurrence of the special combination with an otherwise unused value (say, "X") of the LSB selector bits 121, and having a suitably located MUX (not shown) responsive to "X" that switches in the value of zero in place of any other output.

We turn now to a discussion of how the corduroy artifact of parallel flow can be eliminated. The elimination occurs in the lateral detection strength filter ROM 85, and is accomplished by equipping that filter with a radial-to-radial weighting scheme that meets certain criteria. In brief, the fix is to weight the odd numbered radials in the aperture of the lateral detection strength filter such that the sum of those weights equals the sum of the weights of the even numbers radials in the aperture of the lateral detection strength filter.

Recall that the lateral detection strength filter is the "five across" part of a seven deep by five across spatial aperture in the detection strength spatial filter. The five across are, for one of the seven depths, parts of five consecutive radials. Let these five be named R1–R5. The odd radials are R1, R3 and R5. The even radials are R2 and R4. Note that when the five by seven spatial aperture moves over one radial: the old evens become the new odds (along with a new radial); and, of the old odds one is discarded and the remaining ones become even.

Suppose the gain of one group (I) of channels (say, ch. 1–ch. 64) is G1, and that the gain of the other group (II, ch. 65–ch. 128) is G2. Further suppose that no weightings are used; that each radial in the filter aperture contributes equally. Thus, for a first position of the filter aperture we could have 3G1 and 2G2 contributing to the filter output/ threshold, assuming that the odd radials in the filter aperture came from group I and the evens from group II. Let the signals be close to the threshold, and 3G1 might cause the threshold to be exceeded when G1 is greater than G2. Now let the filter aperture move over one location. Now we get 3G2 and 2G1 contributing to the filter output/threshold. The data values might be nearly identical, but because of the gain difference the threshold is not exceeded. But it will be after the next move, and then won't be following the move after that. Corduroy!

Now suppose that the sum of the weightings (for each of even and odd) is K. That is, W1+W3+W5=W2+W4=K. Then for each location it is KG1 and KG2 that do the contributing to the filter output/threshold. The lateral detection strength filter can now longer tell the difference between three odds plus two evens and two odds plus three evens. Hence, the go/no-go decision about whether or not to accept the velocity is no longer conditioned upon any difference between G1 and G2. There still might be some holes in the image, owing to noise. But at least there won't be a picket fence artificially introduced by a gain differential between groups of channels.

Various different weighting schemes are possible. These include:

|     | W1 | W2 | W3 | W4 | W5 |
| --- | --- | --- | --- | --- | --- |
| (1) | 0 | 1 | 2 | 1 | 0 |
| (2) | 1 | 3 | 4 | 3 | 1 |
| (3) | 1 | 2 | 2 | 2 | 1 |
| (4) | 2 | 3 | 2 | 3 | 2 |

Weightings (1)–(3) are examples of center weightings. Example (4) is a notched center. Other weightings might be desirable, say, for edge extraction.

Finally, it should be appreciated that it needn't necessarily be detection strength that is being filtered with such weightings to remove corduroy. Detection strength is a superb choice, but it could also be simply amplitude, for example.

Also, it should be noted that the weighted filter corduroy removal mechanism described above is not limited only to cases where there is a two to one ratio between receive lines and transmit lines; it can be used with larger ratios as well. Suppose, for example, that the ratio was four to one. Assuming that the lateral aperture of the filter remains five, the following weighting relationship would cure corduroy:

$$W1+W5=W2=W3=W4=K \quad (5)$$

We claim:

1. An ultrasound system wherein a digital representation of acoustic reflection data along acoustic radials, the data including a magnitude derived from a strength of reflection and a velocity derived from a doppler shift, is stored as digital values in a memory for radial processing in the dimension of increasing depth and for lateral processing in the dimension of constant depth, the ultrasound system comprising:

a magnitude input coupled to receive magnitude values that are representations by digital signals of magnitudes derived from strength of reflection;

a velocity input coupled to receive velocity values that are representations by digital signals of velocities derived from doppler shift;

a mapping circuit coupled to consecutive pairs of magnitude and velocity values that, within each pair, correspond to one another, and that produces therefrom consecutive confidence parameter values that are a selected function of both the magnitude value and the velocity value;

a radial confidence parameter filter coupled to the consecutive confidence parameter values and producing therefrom radially filtered digital confidence values;

a radial velocity filter coupled to the velocity values and producing therefrom radially filtered digital velocity values;

a memory that writes and reads the radially filtered digital confidence values and the radially filtered digital velocity values, and having a storage capacity sufficient to do so for a selected number of consecutive acoustic radials;

a lateral confidence parameter filter coupled to the radially filtered digital confidence values stored in the memory and producing therefrom a confidence indicator;

a lateral velocity filter coupled to the radially filtered digital velocity values stored in the memory and producing therefrom laterally filtered digital velocity values; and a gating circuit coupled to the confidence indicator and to the laterally filtered digital velocity values, the gating circuit passing the laterally filtered digital velocity values to an output when the confidence indicator has a first logical value and substituting instead a selected value to be passed to the output when the confidence indicator has a second logical value.

2. In an ultrasound system utilizing parallel flow, a method of eliminating a display artifact produced by differing gains in the separate groups of channels that belong to disparate parallel signal paths, the method comprising the steps of:

representing, during consecutive periods of time, respective data from the disparate parallel signal paths of differing gains as a data signal;

filtering the data signal;

representing as a confidence signal, during the consecutive periods of time, the respective likelihoods that the dam from the corresponding disparate signal paths are valid;

filtering the confidence signal using an aperture that is an odd number of consecutive confidence signals in width, the odd number being at least three, and applying a weighting to the confidence signals in the aperture, the sums of the weightings associated with each disparate path each being equal; and conditioning the use of the value of the filtered data signal based upon the filtered confidence signal; and displaying an ultrasound system image corresponding to the filtered data signal as conditioned upon the filtered confidence signal.

* * * * *

UNITED STATES PATENT AND TRADEMARK OFFICE
CERTIFICATE OF CORRECTION

PATENT NO. : 5,515,852
DATED : May 14, 1996
INVENTOR(S) : Sidney M. Karp, et. al.

It is certified that error appears in the above-indentified patent and that said Letters Patent is hereby corrected as shown below:

Col. 5, line 49, "variance,too" should read --variance, too--.
Col. 6, line 49, Change "oh." (both occurrences) to --ch.
Col. 18, Claim 2, line 47, delete "dam" and insert therefor --data--.

Signed and Sealed this

Eleventh Day of March, 1997

Attest:

BRUCE LEHMAN

Attesting Officer    Commissioner of Patents and Trademarks